United States Patent [19]

Gibeault

[11] Patent Number: 5,271,263
[45] Date of Patent: Dec. 21, 1993

[54] FLUID SAMPLER FOR DETECTION AND MONITORING OF FAILURE CONDITIONS IN FLUID INSULATED ELECTRICAL EQUIPMENT

[76] Inventor: Jean-Pierre Gibeault, 179, Brunswick Boulevard, Pointe-Claire, Quebec, Canada, H9R 5N2

[21] Appl. No.: 982,360

[22] Filed: Nov. 27, 1992

Related U.S. Application Data

[63] Continuation of Ser. No. 690,368, Apr. 24, 1991, abandoned.

[30] Foreign Application Priority Data

Apr. 25, 1990 [CA] Canada .............................. 2015391

[51] Int. Cl.$^5$ ........................ G01N 1/14; G01N 33/26
[52] U.S. Cl. ................................ 73/19.12; 73/863.81; 73/863.83
[58] Field of Search ............ 73/863.81, 863.83, 863.84, 73/19.12

[56] References Cited

U.S. PATENT DOCUMENTS

| | | | |
|---|---|---|---|
| 2,356,845 | 8/1944 | Hines | 73/863.81 |
| 2,836,068 | 5/1954 | Clift | 73/421 |
| 3,751,880 | 8/1973 | Holm | 55/158 |
| 3,844,160 | 10/1974 | Yamaoka | 73/19.1 |
| 3,960,500 | 6/1976 | Ross et al. | 73/863.81 |
| 3,969,608 | 7/1976 | Day | 222/146.5 |
| 3,992,155 | 11/1976 | Nilsson | 23/254 E |
| 4,015,479 | 4/1977 | Apple | 73/863.81 |
| 4,037,475 | 7/1977 | Topham | 73/863.01 |
| 4,096,734 | 6/1978 | Khayat | 73/863.81 |
| 4,112,737 | 9/1978 | Morgan | 55/158 |
| 4,115,229 | 9/1978 | Capone | 73/23.31 |
| 4,188,818 | 2/1980 | Garrison | 73/40.7 |
| 4,192,174 | 3/1980 | Lobermann et al. | 340/646 |
| 4,236,404 | 12/1980 | Ketchum et al. | 73/23.1 |
| 4,271,474 | 6/1981 | Belanger et al. | 364/500 |
| 4,293,399 | 10/1981 | Belanger et al. | 204/195 P |
| 4,373,375 | 2/1983 | Terhune et al. | 73/19.1 |
| 4,402,211 | 9/1983 | Sugawara et al. | 73/19.01 |
| 4,409,814 | 10/1983 | Onuma et al. | 73/19.05 |
| 4,420,687 | 12/1983 | Martinez et al. | 250/343 |
| 4,444,040 | 4/1984 | Sakai et al. | 73/19.10 |
| 4,502,320 | 3/1985 | Sakai et al. | 73/19 |
| 4,578,244 | 3/1986 | Cosgrove, Jr. et al. | 73/863.81 |
| 4,586,390 | 5/1986 | Helke | 73/863.81 |
| 4,604,166 | 8/1986 | Weinberg et al. | 204/1 T |
| 4,669,321 | 6/1987 | Meyer | 73/863.85 |
| 4,715,236 | 12/1987 | Willert | 73/863.86 |
| 4,726,315 | 2/1988 | Bell et al. | 114/244 |
| 4,736,639 | 4/1988 | Averette | 73/863.81 |
| 4,763,514 | 8/1988 | Naito et al. | 73/19.1 |
| 4,764,344 | 8/1988 | Knab | 422/89 |
| 4,772,790 | 9/1988 | Aldridge | 250/343 |
| 4,790,291 | 12/1988 | Barrett | 126/362 |
| 4,917,142 | 4/1990 | Laing et al. | 137/337 |
| 4,928,536 | 5/1990 | Welker | 73/863.83 |
| 4,934,201 | 6/1990 | Grimminger et al. | 73/864.81 |
| 4,942,772 | 7/1990 | Welker | 73/863.83 |
| 5,003,830 | 4/1991 | Spencer | 73/863.83 |
| 5,012,672 | 5/1991 | McKee | 73/19.12 |
| 5,070,738 | 12/1991 | Morgan | 73/863.84 |
| 5,085,087 | 2/1992 | Franck et al. | 73/863.81 |

FOREIGN PATENT DOCUMENTS

| | | | |
|---|---|---|---|
| 1054223 | 5/1979 | Canada . | |
| 2143045 | 8/1971 | Fed. Rep. of Germany | 73/863.84 |
| 2441844 | 11/1976 | Fed. Rep. of Germany | 73/863.83 |
| 0135692 | 11/1978 | Japan | 73/864.34 |
| 0691725 | 10/1979 | U.S.S.R. | 73/863.81 |

Primary Examiner—Robert Raevis
Assistant Examiner—George Dombroske
Attorney, Agent, or Firm—Ronald S. Kosie; Robert Brouillette

[57] ABSTRACT

An apparatus for sampling and analyzing the fluid in an electrical system such as a transformer, a circuit breaker, a reactance or another electrical apparatus using a dielectric fluid as an insulating substance is disclosed. The apparatus includes a device for attaching the apparatus to the electrical system. That device includes at the same time an inlet portion and an outlet portion; a conduit through which the fluid can flow through the apparatus connecting the inlet portion in series to the outlet portion; a pump which can draw the fluid into the apparatus, through the apparatus and expel the fluid back into the electrical system; and a device for attaching a detector for breakdown products, moisture and other parameters indicative of any failure condition in the electrical apparatus.

27 Claims, 1 Drawing Sheet

FLUID SAMPLER FOR DETECTION AND MONITORING OF FAILURE CONDITIONS IN FLUID INSULATED ELECTRICAL EQUIPMENT

FIELD OF THE INVENTION

This is a continuation application of application Ser. No. 07/690,368 filed on Apr. 24, 1991, abandoned.

The present invention relates generally to an improved device for the detection and monitoring of failure conditions in fluid insulated electrical equipment and more particularly to an apparatus for sampling and analyzing such fluid.

BACKGROUND OF THE INVENTION

Systems for detecting fault gases, moisture and breakdown products dissolved in a fluid contained in an electrical system such as a transformer, a circuit breaker or any electric apparatus using a dielectric fluid as an insulating substance are well known in the art and have been described in prior art.

Such systems are described in Canadian Patent no. 1,054,223 (Bélanger), U.S. Pat. No. 4,293,399 (Bélanger et al) and U.S. Pat. No. 4,271,474 (Bélanger et al). For example, the concentration of gaseous hydrogen dissolved in a fluid is determined by a measure of an electric current generated by electro-chemical oxidation of the gaseous hydrogen at an electrode of detection. The prior art detecting and measuring device comprises a polymeric membrane permeable to hydrogen gas in contact with the fluid; an electrolyte capable of producing oxidation of the hydrogen gas diffused through the polymeric membrane at a first electrode and reduction of an oxygen-containing gas such as air at a second electrode; a measuring device connected across the electrode for measuring the intensity of the electrical current generated by the electro-chemical reaction of oxidation of the hydrogen gas, this intensity being proportional to the concentration of hydrogen in the fluid.

Such detection devices are essential to provide an accurate diagnosis of the incorrect operation of transformers, circuit breakers, reactance or any electro-apparatuses using a dielectric fluid such as oil or SF6 gas as insulating substance. It is indeed well-known that, in the event of a disturbance or malfunction of one of the above mentioned apparatuses due to a too high working temperature or a high electrical discharge, there is production of gases in the insulating fluid. Failure conditions may also produce moisture or breakdown products in the insulating fluid. Accordingly, it can be easily understood that the utilization of a device allowing for immediate detection of an increase of the concentration of gases, moisture or breakdown products dissolved in the insulating fluid, is advantageous since it allows immediate diagnosis of the incorrect operation of the electrical apparatus on which the device is mounted, and when this incorrect operation is timely located, to avoid irreparable ruin of the apparatus.

These prior art devices have the drawback that the sample received by the detector may not be uniform or representative of the fluid contained in the electrical system at a given moment in time. For example, in U.S. Pat. No. 4,293,399, the detector is attached to the wall of the electrical apparatus and the fluid must passively diffuse to that area to reach the detector. Such a passive sampling system has two inherent problems. Firstly, the sample that does reach the detector may not be uniform, and secondly if gases, moisture or breakdown products are introduced at some point in the system, which is remote from the detector, it may take considerable time before they will be detected.

Therefore it is desirable to develop a system whereby the sample of the fluid tested is an accurate representation of the actual fluid and the time required to detect gases, moisture or breakdown products is kept to a minimum.

Because such devices are sensitive to temperature fluctuations, it is desirable to provide a means whereby the temperature of the system can be regulated.

It is also desirable that the sampling and detecting apparatus be easily installed onto existing electrical systems.

SUMMARY OF THE INVENTION

The present invention concerns an apparatus used to sample and monitor fluid for the presence of parameters indicative of failure conditions in fluid insulated electrical equipment. This invention may be used to detect the presence of fault gases, moisture and breakdown products contained in the insulating fluid of transformers.

More particularly, this invention describes a more reliable device for sampling the fluid whereby the sample of fluid tested is substantially uniform and thus more representative of the actual fluid contained in the electrical system.

The apparatus for sampling and analyzing the fluid in an electrical system for the presence of fault gases, moisture and breakdown products in accordance with this invention comprises:

means for attaching said apparatus to said electrical system; said means comprising an inlet portion and an outlet portion;

conduit means through connecting said inlet portion in series to said outlet portion;

pumping means whereby said fluid can efficiently be drawn into said apparatus from said electrical system, flow through the apparatus and be expelled back into said electrical system;

attaching means for any detector of fault gases, moisture and breakdown products in said fluid;

The surface of the detector which contacts said fluid is preferably disposed perpendicularly to the flow of the fluid in the apparatus. This surface is preferably located immediately after said pumping means.

The pump allows the continuous and uniform flow of the fluid through the sampling and detection apparatus. Furthermore, the expulsion of the tested sample back into the electrical system will create flow and hence mixing of the fluid within the smaller systems. This will ensure that the samples entering such systems are more uniform.

The use of a pump will also allow a greater volume of fluid to be tested per unit time and hence decrease the time required to detect the presence of hydrogen gas in the electrical system.

The detector is preferably installed inside a housing unit whereby the temperature inside said unit can be maintained constant.

OBJECTS OF THE INVENTION

The present invention is easier to adapt to existing electrical systems as it contains only one inlet/outlet port to be attached to the system.

It is an object of this invention to provide an apparatus for sampling and analyzing the fluid in an electrical system which allows for sample to be more representative of the actual fluid contained in the electrical system.

It is a further object of the invention to provide an apparatus which will improve the uniformity of the fluid within the system.

It is a still further object of the invention to provide an apparatus which will decrease the time required to detect the presence of failure conditions in an electrical system.

It is yet another object of the invention to provide means to regulate the operating temperature of the detector.

DESCRIPTION OF A PREFERRED EMBODIMENT

Figure 1:
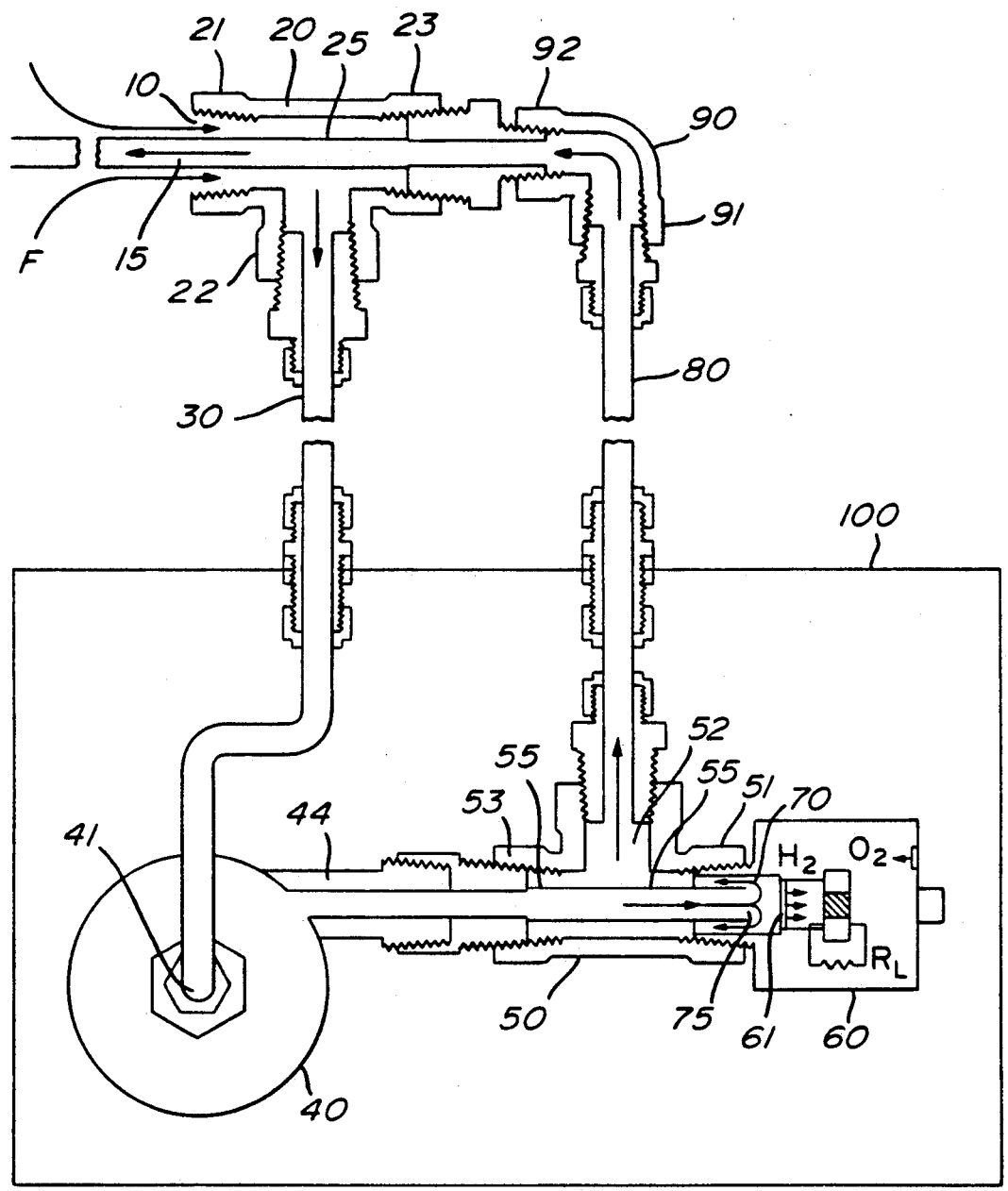
FIG. 1 is a schematic representation of the described apparatus.

Referring generally to FIG. 1, the detector for measuring the concentration of hydrogen gas dissolved in a fluid substance is shown schematically at 60. Such a device is preferably a device manufactured by Syprotec Inc. and sold under its trade mark Hydran.

The improved apparatus for sampling and determining levels of hydrogen gas dissolved in a fluid contained in an electrical system also comprises a special tee 20 comprising combined inlet/outlet 21, an outlet 22 and an inlet 23.

Inlet/outlet 21 is adapted to be attached to a single opening in the electrical system, so that fluid may enter the apparatus in the outer area 10 and exit back into the electrical system through the central area 15. A tube 25 connects said outlet 15 to inlet 23.

Conduit 30 connects outlet 22 of special tee 20 to the inlet 41 of pump 40. The outlet 44 of pump 40 is connected to inlet 51 of special tee 50 which is of a configuration similar to that of special tee 20.

A tube 55 is connected to the inlet 53 of special tee 50, such that the flow of fluid exiting the pump at 44 will continue in a generally straight trajectory until it hits the surface 61 of the detection means 60 which is disposed generally perpendicularly to the flow of said fluid. Thus, the fluid exiting tube 55 at 75 hits the membrane 61 of the detection means 60 and continues in the outer portion 70 of the inlet/outlet 51 of special tee 50. The fluid then exits special tee 50 at outlet 52, which is connected to inlet 23 of special tee 20 by conduit 80 and elbow 90.

The pump and the detection system may be contained in a hollow housing 100. The inside temperature of said housing will be maintained at a predetermined temperature, for example 45° C., to ensure that variation of the temperature of the outside environment will not effect the operation of the detector which can be calibrated at the factory. Tubes 30 and 80 may be secured to said housing by any known means.

The apparatus functions as follows: Fluid (F) from the electrical system enters at 10 into special tee 20 and travels down tube 30 into the pump 40. The pump directs the fluid through tube 55 to the detection system 60. The hydrogen gas in the sample will enter the detection system 60 through the polymeric membrane 61. This membrane is permeable to hydrogen gas and impermeable to the fluid thereby allowing only the hydrogen gas to enter the detection system 60. The detection system 60 functions in a manner similar to the detection systems described in U.S. Pat. Nos. 4,271,474, 4,293,399 and Canadian Patent no. 1,054,223.

The fluid F after deflecting off the membrane 61 will enter special tee 50 and subsequently flow through tube 80 to the outlet tube 25. Outlet tube 25 will be of sufficient length so that it extends far enough into the electrical system to avoid the immediate intake of a sample recently tested.

The pumping unit 40 will not only create current within the sampling system to allow continuous and uniform flow of the sample fluid but in the case of smaller electrical devices, should preferably also create currents within the fluid in the electrical device. This will allow better mixing and hence a more efficient sampling of the fluid contained in the electrical apparatus.

Although a particular embodiment of the invention has been illustrated and described, modification and changes will become apparent to those skilled in the art, and it is intended to cover in the appendant claims such modification and changes has come within the true spirit and scope of the invention. For example, although the detecting device which is described in the preferred embodiment is an hydrogen gas detector, the apparatus of the present inventor may also be used with any other device for detecting other fault gases, moisture and/or breakdown products.

I claim:

1. An apparatus for sampling and analyzing a dielectric liquid in an interior of an electrical system for the presence, in the dielectric liquid, of a fault gas, moisture or a breakdown product, said apparatus comprising:

a fluid conduit loop comprising a mechanical pump, a first end portion and a second end portion, said first and second end portions each having a mouth for liquid communication with said interior of the electrical system, said pump being connected in said fluid conduit loop intermediate said end portions for withdrawing dielectric liquid from said interior of said electrical system through one of said mouths, circulating dielectric liquid through said fluid conduit loop and discharging dielectric liquid back into said interior of the electrical system through the other of said mouths, and detection means for the detection of a fault gas, moisture or a breakdown product in dielectric liquid circulating in said fluid conduit loop, said apparatus being characterized in that said fluid conduit loop consists of a liquid phase conduit loop, said second end portion comprises a first member and a second member, said second member comprising the mouth of said second end portion, the first member of said second end portion is disposed within said first end portion in radially spaced relation therewith, said first and second end portions are configured for connecting said fluid conduit loop to a single dielectric liquid access opening of the electrical system such that, when the fluid conduit loop is connected to said liquid access opening, the mouths of said first and second end portions communicate with said interior of the electrical system, the second member of the second end portion projects beyond the mouth of the first end portion, and the mouth of the second end portion is disposed in said dielectric liquid remote from the mouth of the first end portion so as to inhibit the same portion of dielectric liquid being discharged back into the electrical system, from being recirculated through the fluid conduit loop, and said detection means comprises a member having a surface configured for isolating a fault gas, moisture or a breakdown product from the dielectric liquid, said surface being disposed so as to contact dielectric liquid circulating through said fluid conduit loop.

2. An apparatus as defined in claim 1 wherein said second end portion is disposed concentrically within said first end portion.

3. An apparatus as defined in claim 1 wherein said pump is configured to create enough pressure so as to promote circulation of the dielectric liquid in the electrical system.

4. An apparatus as defined in claim 1 wherein said detection means is contained within a hollow housing unit comprising means to maintain the temperature inside said housing unit at a predetermined temperature.

5. A combination as defined in claim 4 wherein said pump is contained within said housing unit.

6. An apparatus for sampling and analyzing a dielectric liquid in an interior of an electrical system for the presence, in the dielectric liquid, of a fault gas, said apparatus comprising:

a fluid conduit loop comprising a mechanical pump, a first end portion and a second end portion, said first and second end portions each having a mouth for liquid communication with said interior of the electrical system, said pump being connected in said fluid conduit loop intermediate said end portions for withdrawing dielectric liquid from said interior of the electrical system through one of said mouths, circulating dielectric liquid through said fluid conduit loop and discharging dielectric liquid back into said interior of the electrical system through the other of said mouths, and detection means for the detection of a fault gas in dielectric liquid circulating through said fluid conduit loop, said apparatus being characterized in that said fluid conduit loop consists of a liquid phase conduit loop, said second end portion comprises a first member and a second member, said second member comprising the mouth of said second end portion, the first member of said second end portion is disposed within said first end portion in radially spaced relation therewith, said first and second end portions are configured for connecting said fluid conduit loop to a single dielectric liquid access opening of the electrical system such that, when the fluid conduit loop is connected to said liquid access opening, the mouths of said first and second end portions communicate with said interior of the electrical system, the second member of the second end portion projects beyond the mouth of the first end portion, and the mouth of the second end portion is disposed in said dielectric liquid remote from the mouth of the first end portion so as to inhibit the same portion of dielectric liquid being discharged back into the electrical system, from being recirculated through the fluid conduit loop, and said detection means comprises a membrane, for isolating the fault gas from the dielectric liquid, said membrane being permeable to said fault gas and impermeable to said dielectric liquid and said membrane being disposed so as to contact dielectric liquid circulating through said fluid conduit loop.

7. An apparatus as defined in claim 6, wherein said membrane is disposed perpendicularly to the flow of dielectric liquid.

8. An apparatus as defined in claim 6 wherein said second end portion is disposed concentrically within said first end portion.

9. An apparatus as defined in claim 8, wherein said membrane is disposed perpendicularly to the flow of dielectric liquid.

10. An apparatus as defined in claim 6 wherein said pump is configured to create enough pressure so as to promote circulation of the dielectric liquid in the electrical system.

11. An apparatus as defined in claim 6, wherein said second end portion is disposed concentrically within said first end portion, wherein said pump is configured to create enough pressure so as to promote circulation of the dielectric liquid in the electrical system and wherein said membrane is disposed perpendicularly to the flow of dielectric liquid.

12. An apparatus as defined in claim 11 wherein said detection means is contained within a hollow housing unit comprising means to maintain the temperature inside said housing unit at a predetermined temperature.

13. An apparatus as defined in claim 6 wherein said detection means is contained within a hollow housing unit comprising means to maintain the temperature inside said housing unit at a predetermined temperature.

14. In combination an electrical system comprising a dielectric liquid in an interior thereof, said electrical system comprising a liquid access opening for communication with said interior of the electrical system, and an apparatus for sampling and analyzing said dielectric liquid for the presence, in the dielectric liquid, of a fault gas, moisture or a breakdown product, said apparatus comprising:

a fluid conduit loop comprising a mechanical pump, a first end portion and a second end portion, said first and second end portions each having a mouth for liquid communication with said interior of the electrical system, said pump being connected in said fluid conduit loop intermediate said end portions for withdrawing dielectric liquid from said interior of said electrical system through one of said mouths, circulating dielectric liquid through said fluid conduit loop and discharging dielectric liquid back into said interior of the electrical system through the other of said mouths, and detection means for the detection of a fault gas, moisture or a breakdown product in dielectric liquid circulating in said fluid conduit loop, said apparatus being characterized in that said fluid conduit loop consists of a liquid phase conduit loop, said second end portion comprises a first member and a second member, said second member comprising the mouth of said second end portion, the first member of said second end portion is disposed within said first end portion in radially spaced relation therewith, said fluid conduit loop is connected to said liquid access opening such that the mouths of said first and second end portions communicate with said interior of the electrical system, the second member of the second end portion projects beyond the mouth of the first end portion, and the mouth of the second end portion is disposed in said dielectric liquid remote from the mouth of the first end portion so as to inhibit the same portion of dielectric liquid being discharged back into the electrical system, from being recirculated through the fluid conduit loop, and said detection means comprises a member having a surface configured for isolating a fault gas, moisture or a breakdown product from the dielectric liquid, said surface being disposed so as to contact dielectric liquid circulating through said fluid conduit loop.

15. A combination as defined in claim 14 wherein said second end portion is disposed concentrically within said first end portion.

16. A combination as defined in claim 14 wherein said pump is configured to create enough pressure so as to promote circulation of the dielectric liquid in the electrical system.

17. A combination as defined in claim 14, wherein said detection means is contained within a hollow housing unit comprising means to maintain the temperature inside said housing unit at a predetermined temperature.

18. A combination as defined in claim 17 wherein said pump is contained within said housing unit.

19. In combination an electrical system comprising a dielectric liquid in an interior thereof, said electrical system comprising a liquid access opening for communication with said interior of the electrical system, and an apparatus for sampling and analyzing said dielectric liquid for the presence, in the dielectric liquid, of a fault gas, said apparatus comprising:

a fluid conduit loop comprising a mechanical pump, a first end portion and a second end portion, said first and second end portions each having a mouth for liquid communication with said interior of the electrical system, said pump being connected in said fluid conduit loop intermediate said end portions for withdrawing dielectric liquid from said interior of the electrical system through one of said mouths, circulating dielectric liquid through said fluid conduit loop and discharging dielectric liquid back into said interior of the electrical system through the other of said mouths, and detection means for the detection of a fault gas in dielectric liquid circulating through said fluid conduit loop, said apparatus being characterized in that said fluid conduit loop consists of a liquid phase conduit loop, said second end portion comprises a first member and a second member, said second member comprising the mouth of said second end portion, the first member of said second end portion is disposed within said first end portion in radially spaced relation therewith, said fluid conduit loop is connected to said liquid access opening such that the mouths of said first and second end portions communicate with said interior of the electrical system, the second member of the second end portion projects beyond the mouth of the first end portion, and the mouth of the second end portion is disposed in said dielectric liquid remote from the mouth of the first end portion so as to inhibit the same portion of dielectric liquid being discharged back into the electrical system, from being recirculated through the fluid conduit loop, and said detection means comprises a membrane, for isolating the fault gas from the dielectric liquid, said membrane being permeable to said fault gas and impermeable to said dielectric liquid and said membrane being disposed so as to contact dielectric liquid circulating through said fluid conduit loop.

20. A combination as defined in claim 19, wherein said membrane is disposed perpendicularly to the flow of dielectric liquid.

21. A combination as defined in claim 19 wherein said second end portion is disposed concentrically within said first end portion.

22. A combination as defined in claim 21 wherein said membrane is disposed perpendicularly to the flow of dielectric liquid.

23. A combination as defined in claim 19 wherein said pump is configured to create enough pressure so as to promote circulation of the dielectric liquid in the electrical system.

24. A combination as defined in claim 19, wherein said second end portion is disposed concentrically within said first end portion, wherein said pump is configured to create enough pressure so as to promote circulation of the dielectric liquid in the electrical system and wherein said membrane is disposed perpendicularly to the flow of dielectric liquid.

25. A combination as defined in claim 24 wherein said detection means is contained within a hollow housing unit comprising means to maintain the temperature inside said housing unit at a predetermined temperature.

26. A combination as defined in claim 19 wherein said detection means is contained within a hollow housing unit comprising means to maintain the temperature inside said housing unit at a predetermined temperature.

27. An apparatus for sampling and analyzing a dielectric oil in an interior of an electrical system for the presence, in the dielectric oil, of a fault gas, moisture or a breakdown product, said apparatus comprising:

a fluid conduit loop comprising a mechanical pump, a first end portion and a second end portion, said first and second end portions each having a mouth for liquid communication with said interior of the electrical system, said pump being connected in said fluid conduit loop intermediate said end portions for withdrawing dielectric oil from said interior of said electrical system through one of said mouths, circulating dielectric oil through said fluid conduit loop and discharging dielectric oil back into said interior of the electrical system through the other of said mouths, and detection means for the detection of a fault gas, moisture or a breakdown product in dielectric oil circulating in said fluid conduit loop, said apparatus being characterized in that said fluid conduit loop consists of a liquid phase conduit loop, said second end portion comprises a first member and a second member, said second member comprising the mouth of said second end portion, the first member of said second end portion is disposed within said first end portion in radially spaced relation therewith, said first and second end portions are configured for connecting said fluid conduit loop to a single dielectric oil access opening of the electrical system such that, when the fluid conduit loop is connected to said oil access opening, the mouths of said first and second end portions communicate with said interior of the electrical system, the second member of the second end portion projects beyond the mouth of the first end portion, and the mouth of the second end portion is disposed in said dielectric oil remote from the mouth of the first end portion so as to inhibit the same portion of dielectric oil being discharged back into the electrical system, from being recirculated through the fluid conduit loop, and said detection means comprises a member having a surface configured for isolating a fault gas, moisture or a breakdown product from the dielectric oil, said surface being disposed so as to contact dielectric oil circulating through said fluid conduit loop.

* * * * *